US006986280B2

(12) United States Patent
Muckenhirm (10) Patent No.: US 6,986,280 B2
(45) Date of Patent: Jan. 17, 2006

(54) INTEGRATED MEASURING INSTRUMENT (75) Inventor: Sylvain G. Muckenhirm, Santa Barbara, CA (US)

(73) Assignee: Fei Company, Hillsboro, OR (US)

( * ) Notice: Subject to any disclaimer, the term of this patent is extended or adjusted under 35 U.S.C. 154(b) by 53 days.

(21) Appl. No.: 10/317,160

(22) Filed: Dec. 11, 2002

(65) Prior Publication Data
US 2003/0168594 A1 Sep. 11, 2003

Related U.S. Application Data (60) Provisional application No. 60/350,778, filed on Jan. 22, 2002.

(51) Int. Cl.
G01N 13/10 (2006.01)

(52) U.S. Cl. ............... 73/104; 73/105; 250/306; 250/307; 250/492.2; 356/634; 356/635; 356/636

(58) Field of Classification Search ............... 73/104, 73/105; 250/306, 307, 491.1, 492.1; 356/600, 356/601, 604, 625, 634, 635, 636
See application file for complete search history.

(56) References Cited

U.S. PATENT DOCUMENTS

| 4,408,884 | A | * | 10/1983 | Kleinknecht et al. ....... 356/496 |
| 5,091,320 | A | | 2/1992 | Aspnes et al. .................. 437/8 |
| 5,164,790 | A | | 11/1992 | McNeil et al. ............... 356/355 |
| 5,216,235 | A | * | 6/1993 | Lin ........................ 250/201.6 |
| 5,262,643 | A | | 11/1993 | Hammond et al. ......... 250/306 |
| 5,307,693 | A | | 5/1994 | Griffith et al. ........... 73/862.68 |
| 5,362,585 | A | * | 11/1994 | Adams ........................ 430/30 |
| 5,394,500 | A | | 2/1995 | Marchman ................. 385/123 |
| 5,501,637 | A | * | 3/1996 | Duncan et al. ............. 374/126 |
| 5,517,027 | A | | 5/1996 | Nakagawa et al. | |
| 5,699,447 | A | * | 12/1997 | Alumot et al. .............. 382/145 |
| 5,739,909 | A | | 4/1998 | Blayo et al. ................. 356/369 |
| 5,756,887 | A | | 5/1998 | Bryson, III et al. .......... 73/105 |
| 5,801,381 | A | | 9/1998 | Flecha et al. ............... 250/306 |
| 5,835,221 | A | * | 11/1998 | Lee et al. .................... 356/369 |
| 5,955,654 | A | * | 9/1999 | Stover et al. ................ 73/1.89 |
| 6,016,684 | A | | 1/2000 | Scheer et al. | |

(Continued)

FOREIGN PATENT DOCUMENTS

| EP | 0884 617 | 12/1998 |
| EP | 0 928 950 | 7/1999 |
| WO | WO01/06516 A1 | 1/2001 |

OTHER PUBLICATIONS

Borghesi et al., "Influence of Roughness and Grain Dimension on the Optial Functions of Polycrystalline Silicon Films", 1998, Thin Solid Films, vols. 313-314, pp. 243-247.*

(Continued)

Primary Examiner—Hezron Williams
Assistant Examiner—David A. Rogers
(74) Attorney, Agent, or Firm—Michael O. Scheinberg (57) ABSTRACT A surface analyzing system including in one system both an integrating optical instrument, such as a scatterometer, and individual-feature-measuring instrument, such as a scanning probe microscope or a beam imaging system, for example, a scanning electron microscope. In a preferred embodiment, the two instruments are capable of characterizing a wafer held on a common stage. The stage may be movable a predetermined displacement to allow the same area of the wafer to be characterized by a scatterometer at one position of the stage and to be characterized by the scanning probe microscope or beam imaging system. The scatterometer can rapidly measure wafers to indicate whether a problem exists, and the scanning probe microscope can perform detailed measurements on wafers flagged by the scatterometer.

32 Claims, 5 Drawing Sheets

U.S. PATENT DOCUMENTS

| | | | | |
|---|---|---|---|---|
| 6,229,609 | B1 | 5/2001 | Muramatsu et al. | |
| 6,407,373 | B1 * | 6/2002 | Dotan | 250/201.3 |
| 6,421,457 | B1 * | 7/2002 | Su | 382/149 |
| 6,522,776 | B1 * | 2/2003 | Ehrichs | 382/144 |
| 6,552,337 | B1 * | 4/2003 | Cho et al. | 250/307 |
| 6,658,922 | B2 * | 12/2003 | Leigh et al. | 73/105 |
| 6,743,646 | B2 * | 6/2004 | Jakatdar et al. | 438/16 |
| 6,744,057 | B2 * | 6/2004 | Tanaka et al. | 250/491.1 |
| 6,744,648 | B2 * | 6/2004 | Chen | 363/98 |
| 2001/0008272 | A1 * | 7/2001 | Rinn | 250/491.1 |
| 2002/0149782 | A1 * | 10/2002 | Raymond | 356/616 |
| 2002/0165636 | A1 * | 11/2002 | Hasan | 700/121 |
| 2003/0133104 | A1 * | 7/2003 | Niu et al. | 356/237.5 |
| 2003/0194820 | A1 * | 10/2003 | Jakatdar et al. | 438/16 |
| 2004/0018653 | A1 * | 1/2004 | Johnson et al. | 438/16 |
| 2004/0070772 | A1 * | 4/2004 | Shchegrov et al. | 356/625 |
| 2004/0080757 | A1 * | 4/2004 | Stanke et al. | 356/601 |
| 2004/0109165 | A1 * | 6/2004 | Fay et al. | 356/508 |
| 2004/0147048 | A1 * | 7/2004 | Jakatdar et al. | 438/16 |

OTHER PUBLICATIONS

Lohner et al., "Surface Disorder Production During Plasma Immersion Implantation", 1998, Thin Solid Films, vols. 313-314, pp. 254-258.*

Petrik et al., "Comparative Study of Polysilicon-on-oxide Using Spectroscopic Ellipsometry, Atomic Force Microscopy, and Transmission Electron Microscopy", 1998, Thin Solid Films, vols. 313-314, pp. 259-263.*

Nayar et al., "The Surface Roughness and Optical Properties of High Quality Si Epitaxial Layers", 1993, Thin Solid Films, vol. 233, pp. 40-45.*

Tian et al., "Optical Spectra of a Conducting Polymer (Polymethyl-3-thiophene) at Several Stages of the Electrodeposition Process", 1993, Thin Solid Films, vol. 233, pp. 91-95.*

Orloff et al., "Ex Situ Variable Angle Spectroscopic Ellipsometry Studies of Electron Cyclotron Resonance Etching of Hg1-xCdxTe", 1993, Thin Solid Films, vol. 233, pp. 46-49.*

Ducharme et al., "A Self-Calibrating Modulation Ellipsometer", 1996, SPIE Proceedings, vol. 2839.*

Allgair et al., "Spectroscopic Critical Dimension Metrology for CD Control and Stepper Characterization", Yield Management Solutions, Fall 2001, pp. 50-55.*

"Manufacturing Considerations for Implementation of Scatterometry for Process Monitoring," Proc. Of the SPIE Conference on Metrology, Inspection, and Process Control for Microlithography XIV, Feb. 28, 2000-Mar. 2, 2000.

W. Pfeiffer, F. Sattler, S. Vogler, G. Gerber, J-Y. Grand, and R. Moller, "Photoelectron Emission In Femtosecond Laser Assisted Scanning Tunneling Microscopy" Applied Physics B Laser Optics B64, 265-268 (1997).

Thomas Netsch and Heinz-Otto Peitgen "Scale-Space Signatures for hte Detection of Clustered Microcalcifications in Digital Mammograms" IEEE Transactions on Medical imaging, Vo. 18, No. 9, Sep. 1999.

* cited by examiner

ND MEASURING INSTRUMENT

This application claims priority from U.S. Provisional Patent Application No. 60/350,778, filed on Jan. 22, 2002.

TECHNICAL FIELD OF THE INVENTION

The invention relates generally to systems for measuring microscopic surface features and, in particular, to the integration of an integrating optical instrument, such as a scatterometer, with an instrument that measures individual features, such as a scanning probe microscope or a scanning electron microscope.

BACKGROUND OF THE INVENTION

The fabrication of advanced integrated circuits requires the formation of extremely small, precise features on a semiconductor wafer. Such features are typically formed first by a photolithography process in temporary layers of photoresist, and the photoresist features are then used to create permanent structures on the wafer. For example, holes are formed in insulating layers and later filled with a conductive material to create connections between layers in a circuit. Trenches are also formed in insulating layers and later filled with a conductive material to form capacitors. Groups of thin conductive lines are formed to make buses to carry signals from one area of a chip to another. The groups of conductors are characterized by the width of each conductor and a pitch, that is, the distance between the conductors.

As the precision requirements for semiconductor processing increases, there is a need to constantly monitor the fabrication process to ensure that it is meeting the stringent requirements. In some cases, every wafer going through the fabrication line is measured in what is sometimes referred to as in-line metrology. Engineers may monitor both the features on the temporary photoresist layer and the permanent features created on the wafer. Features on the wafer are three-dimensional structures and a complete characterization must describe not just a surface dimension, such as the top width of a hole or conductor, but a complete three-dimensional profile of the feature. For example, although an ideal feature typically has vertical sidewalls, the actual sidewalls may have excessive slope that narrows or widens the feature below its top surface. Process engineers must be able to accurately measure the profiles of such surface features to fine tune the fabrication process and assure a desired device geometry is obtained.

During process development, one method of characterizing the fabrication process results is by sectioning, that is, cutting a wafer through the feature to be characterized, and then observing the exposed cross section using a scanning electron microscope (SEM). While useful in developing new processes, this method is less useful in monitoring production processes because the entire wafer is destroyed to measure a feature. Moreover, it is time consuming to section the wafer at the correct position and view it in an SEM.

Three processes that are often used for such in-line metrology are critical dimension scanning electron microscopy (CD SEM), scanning probe microscopy (SPM), and scatterometry. CD SEM entails using a scanning electron microscope to create an image of the top surface of the wafer being processed. CD SEM is particularly useful in monitoring the critical dimensions, such as the top width of a hole or trench or the width of conductors. Because it displays a top view, CD SEM does not usually provide any information on the three-dimensional profile of such holes or conductors, and may not alert a process engineer if the sidewalls of a feature are deviated from the vertical.

Insulators and photoresist tend to become electrically charged by the electrons in the CD SEM, and this charging causes the edges of the feature image to blur, making measurements uncertain by between 2 nm and 25 nm. The edge blurring effect can be characterized by measuring features having known dimensions and subsequent CD SEM measurements can be partially compensated to correct for the edge blurring. However, the charging is dependent upon the composition and thickness of a number of the layers underlying the feature. If the device design changes or even if the process for the underlying layers drifts, a separate set of calibrations is required.

A further drawback with electron microscopy is that the measurement needs to be performed in a high vacuum to prevent the probing electrons from being scattered by air molecules. It takes considerable time to remove the air from an SEM sample chamber, thereby preventing rapid feedback and limiting the number of wafers that can be measured.

The second method of in-process measurements, SPM, uses a very small probe tip that is scanned across the wafer surface. There are many types of SPMs, including scanning tunneling microscopes and several types of atomic force microscopes (AFM). In one type of AFM used in semiconductor processing, the probe tip is moved vertically and horizontally into contact or near contact with the surface. The vertical positions at or near contact are tabulated and provide a profile of the surface. AFMs have been demonstrated to achieve resolution of the order of 1 nm, which is adequate for most advanced processes, and they can be operated at atmospheric pressure.

However, AFMs suffer from low throughput. AFMs require not only horizontal scanning, but also some type of vertical scanning. The vertical scanning can be substantially reduced by a feedback control of an oscillatory vibration of the tip operated in the non-contact mode, but sharply profiled features reduce this advantage. It is difficult to initially align the probe tip with nanometer-size feature. As a result, except when measuring test patterns in the shape of gratings, a large number of parallel scans must be performed to assure that the probe encounters the feature. It can take several minutes to make measurements across one feature and several hours to measure a 50 $\mu$m square area. For these reasons, AFMs in production operation can profile only a limited area of the chip.

The third type of in-process inspection methods, generally referred to as scatterometry, entails directing light onto a test pattern on a surface and measuring the reflected light. The reflected light is affected by the geometry and composition of the target. For example, the results are affected by the width and spacing of repetitive features, the composition of the material at and below the surface, including the thickness of any layers near the surface. The result of a scatterometer measurement is typically a "signature" or graph, showing the variation in the intensity of the reflected light as the wavelength or the angle of incidence changes.

Because scatterometry requires a regular grid to create the diffractive effect measured, when scatterometry is used to determine dimensions, it is typically used on isolated test patterns, rather than on the circuit itself. The test patterns are created on unused portions of the wafers, typically between the individual integrated circuits, at the same time that the actual circuits are created so that the test patterns reflect the processes that are creating the actual production product, that is, the integrated circuits. The test patterns typically consist of a grating pattern about 50 μm×50 μm. Scatterometry uses a relatively wide beam of light and provides average information about the geometry over the area of the beam. Thus, rather than determining the width of a particular line or feature, scatterometry determines, for example, the average line width over the smaller of the spot size of the optical assembly or the test pattern. An optical instrument, such as a scatterometer, that integrates information from multiple features to produce a result is referred to as an integrating optical instrument, as opposed to an individual-feature-measuring instrument, such as an AFM, SEM, or focused ion beam system, that measured a characteristic of a single feature.

Typically, scatterometry is practiced with an ellipsometer or a reflectometer in which a probing beam of radiation having a diameter of about 25 μm to about 200 μm strikes the test grating pattern at a fixed angle with respect to the surface normal and to the grating structure axes. A polarization-sensitive optical detection system is arranged to detect the radiation reflected from the surface. There are two general approaches to the types of ellipsometric data used for scatterometry. In a first approach, referred to as spectroscopic scatterometry, the optical detector is set to detect a beam reflected at a complementary angle about the surface normal, that is, a first-order reflection, and the data is obtained over a range of wavelengths of incident light. The acquired data may simply be the spectrally resolved intensity, or it may be the dual sets of data possible in ellipsometry, for example, the spectrally resolved $\Psi$ and $\Delta$ parameters well known in ellipsometry. In a second approach, referred to angle-resolved scatterometry, a single wavelength is used, but the detector is scanned over a range of angles. In either case, the ellipsometer produces at least one distinctive trace over either wavelength or angle.

Scatterometry is well suited to process control. It nondestructively probes the wafer so that the wafer can be returned to the production line, and it can be performed at atmospheric pressure with equipment occupying relatively little space. A complete set of scatterometry data can be acquired from a test site in about 200 ms. Moving between test sites on a wafer can be done in less than 3 seconds. Since a typical process sequence in IC fabrication has a throughput of less than one wafer per minute, scatterometry can probe many test sites on every wafer without interrupting the process flow.

The general process for using scatterometry for process control is described by Allgair et al. in "Manufacturing Considerations For Implementation Of Scatterometry For Process Monitoring," Proc. of the SPIE Conference on Metrology, Inspection, and Process Control for Microlithography XIV, Feb. 28–Mar. 2, 2000. It is generally acknowledged that for multi-layer structures, the ellipsometric data cannot be reasonably and directly interpreted to determine the grating structure, or even just the grating pitch, line width, or line spacing ratio. Instead, libraries of data are generated by performing optical scattering calculations for structures in which only some of the parameters are varied and the others are assumed known. For example, one may assume a particular pitch, straight vertical walls, and a particular material composition and layer thickness, and then calculate a set of patterns or graphs based upon different line width. Then, during an actual measurement, the scatterometry graph is compared to the graphs in the library. Although the library information is referred to graphs or patterns, it is understood that the process of generating measurement data and comparing the measurement data to the library data can be performed entirely in software, without producing any actual images of graphs or patterns. The line width parameter of the library graph closest to the experimental data is assumed to be the line width of the measured structure. The closeness may be determined by calculating the root mean square error between each library graph and the experimental data and choosing the library graph with the smallest root mean square error.

This approach, however, assumes that attributes of the test structure that are not being measured, for example, the slope of the vertical walls, the material composition, and the layer thickness, are the same as the attributes assumed in the generation of the library patterns. If some attribute is different, the results are inaccurate and a new library must be calculated. It is generally considered infeasible to consider all possible structures in seeking the structure with the minimum root mean square error. Therefore, scatterometry is limited by the need to assume certain characteristics of the structure to be measured.

In general, scatterometry is good at detecting small changes and variations in processing but ill suited for larger changes because the results of larger changes cannot be matched with library patterns. Although SEMs and atomic force microscopy are effective at detecting significant changes, they are less suited to a production environment. Furthermore, they are relatively insensitive to compositional variations that are important for device reliability.

SUMMARY OF THE INVENTION

An object of the invention is to enhance the efficiency or accuracy of microscopic measurements.

The invention integrates into a single measurement system an integrating optical measurement, such as a scatterometer, and an individual-feature-measuring instrument. The integrating optical measurement can be used to rapidly screen samples, and the individual feature-measuring instrument can be used to measure when the integrating optical measurement instrument identifies a problem. By having both instruments in a single measurement system, a point on a sample can be readily measured by both instruments, preferably with little or no repositioning. The instruments can provide complementary data to provide a more complete characterization of the target, and the instruments can be used to cross check each other.

In an embodiment using a scatterometer and an AFM, for example, the AFM can be used to help interpret, calibrate, and verify the scatterometer. The scatterometer can help verify the AFM and identify when the AFM reaches the limits of its accuracy. The cost of operating each instrument is decreased because using the scatterometer as a screening tool reduces AFM measurement and so reduces wear on the expensive AFM probe tip. The AFM verification of the scatterometer can eliminate premature replacement of the scatterometer light source. The scatterometer could also be used to provide layer thickness and composition information. Other advantages of the integrated instrument are described below.

Similarly, in an embodiment using a scatterometer and a SEM, the SEM can be used to help interpret, calibrate, and verify the scatterometer. The scatterometer can help calibrate and verify the SEM.

Similarly, in an embodiment using a scatterometer and a dual beam system, such as a system including an ion beam and an electron beam, one of the beams of the dual beam can be used to help interpret, calibrate, and verify the scatterometer. The scatterometer can help calibrate and verify the dual beam.

In some embodiments, a substrate to be analyzed is supported on a movable support, and both the scatterometer and AFM or a CD SEM can analyze the substrate on the support. If necessary, the support can move the wafer a predetermined distance between probe positions of the scatterometer and atomic force microscope, thereby reducing or eliminating the time consuming task of locating a target feature using the AFM. In other systems, such as a cluster system, each instrument has its own support.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed could be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and the advantages thereof, reference is now made to the following descriptions taken in conjunction with the accompanying drawings, in which.

DETAILED DESCRIPTION OF THE PREFERRED EMBODIMENTS

The term scatterometer is used herein as a general term to describe any instrument that directs light to a sample and determines characteristics of the sample by measuring light reflected or scattered from the sample. The term includes ellipsometer-based scatterometry, reflectometry, and similar techniques.

The invention combined an integrating optical instrument and an individual-feature-measuring instrument. One embodiment of the invention integrates in a single measurement instrument a scanning probe microscope, such as an AFM and an ellipsometer-based scatterometer. A wafer or other substrate supported on a single stage shared by both instruments can be probed by either the AFM or the scatterometer, either without repositioning the stage or by repositioning the stage by a predetermined offset. Thus, in a preferred embodiment, it is unnecessary to pick up the work piece and move it from one machine to another, thereby eliminating the time-consuming activity of locating the area to be measured on the second machine. Some embodiments use a beam imaging system, such as a scanning electron microscope or a focused ion beam, as the individual-feature-measuring instrument. Some embodiments use an ellipsometer, a scatterometer, or a reflectometer as the integrating optical instrument.

Figure 1:
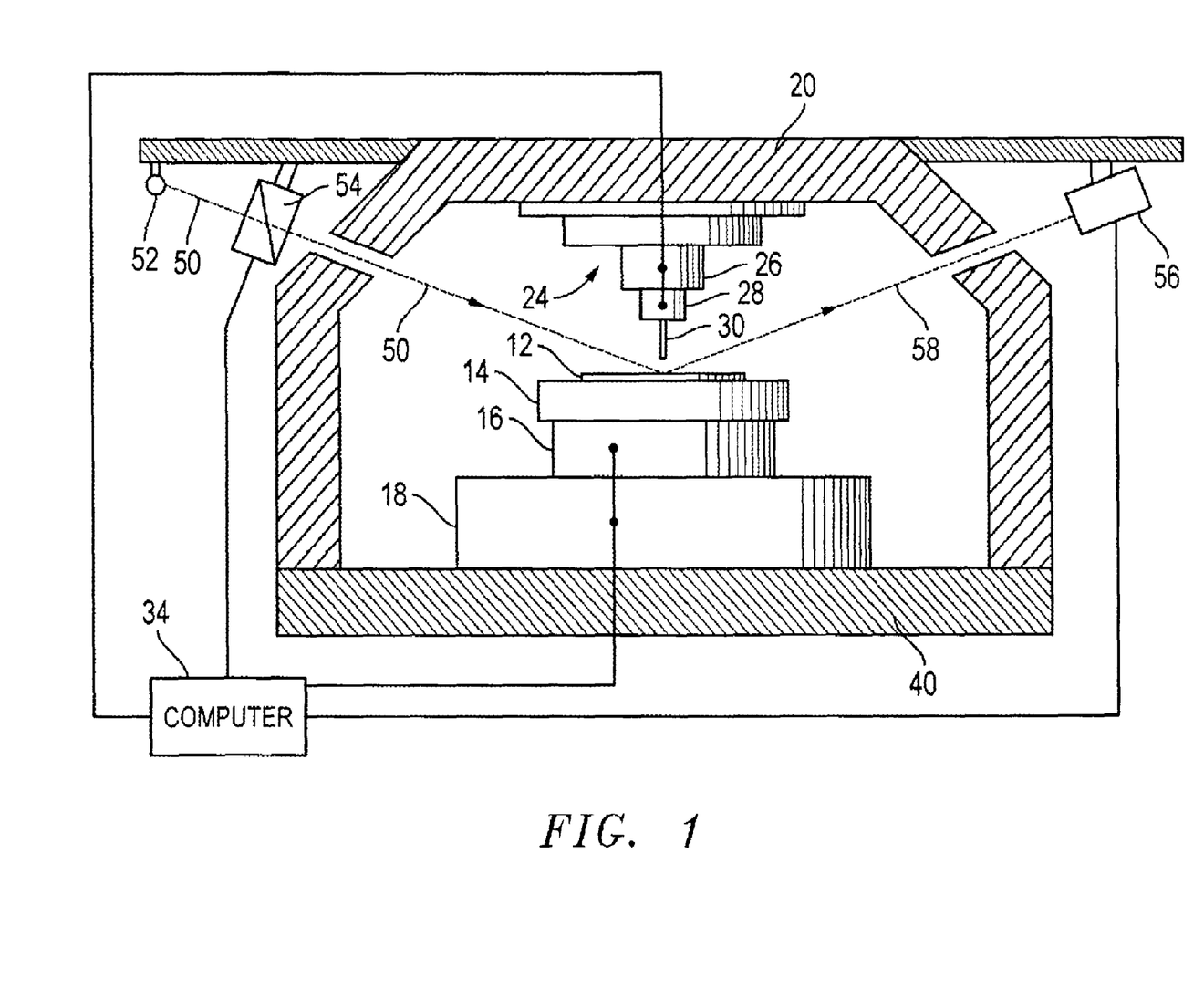
FIG. 1 is a schematic elevational view of a surface analyzer of one embodiment of the invention incorporating both a scatterometer and an atomic force microscope (AFM).

An embodiment is schematically illustrated in the side view of FIG. 1. The parts related to AFM have been disclosed, for example, by Mitchell et al. in U.S. patent application, Ser. No. 09/354,528, filed Jul. 15, 1999, incorporated herein by reference in its entirely. This application has been published as International Publication WO 01/06516-A1. A wafer 12 is supported on a work piece holder 14 that can chuck the wafer 12, for example, mechanically or pneumatically. An x-direction slide 16 and a y-direction slide 18 provide horizontal motion to the wafer 12 allowing any portion of the wafer to be positioned under the test position. If desired an additional z-direction elevator may be included to provide vertical motion to the wafer 12. All of these motions are relatively course compared to the dimension of the features being probed on the wafer 12.

An overhead gantry 20 is supported on a heavy stationary table 40, also supporting the wafer 12 and associated slides and supports. An atomic force microscope (AFM) probe head 24 is supported on the gantry over the wafer 12. It includes a piezoelectric actuator 26 capable of providing about 70 micron of motion in each of the x- and y-directions and 15 $\mu m$ in the z-direction. A probe 28 with a small probe tip 30 is suspended from the actuator 28 so that the probe tip 30 can engage or nearly engage the feature of the wafer 12. A computer 34 controls the slides 16, 18 to move the wafer 12 and also controls the actuator 26 to move the probe tip 30. The computer 34 also monitors the probe 28 that senses the engagement of the probe tip 30 with the wafer 12.

Figure 2:
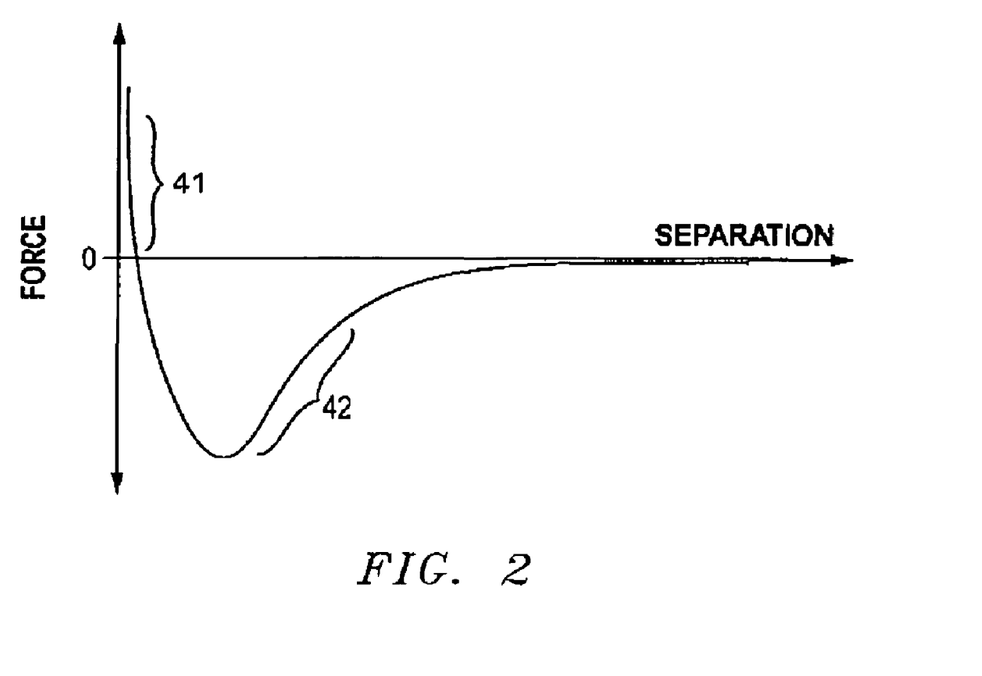
FIG. 2 is a plot of the force exerted on an AFM probe as a function of the separation of the probe tip from the surface being probed.

The probe 28 and its associated probe tip 30 may be of two types. The plot of FIG. 2 schematically illustrates the force experienced by a probe tip as a function of its distance from the sample, that is, the tip-to-sample separation. In the plot, a positive force is a repulsive force, and a negative one is attractive. As the probe tip closely approaches the sample, but without touching it, there is a van der Waals attraction between the tip and sample owing to atomic scale interactions of the electrons of the atoms of tip and sample. The van der Waals force increases in magnitude with decreasing separation. Eventually, however, the probe tip contacts the sample, and the elastic force of engagement produces a rapidly increasing repulsive force that overcomes the van der Waals force.

One type of probe operates in a contact region 41 and records the vertical position of the probe at which the measured repulsive force exceeds a threshold as the probe tip elastically deforms the wafer surface. This type of probe is described by Mitchell et al. in the above-cited patent application and by Griffith et al. in U.S. Pat. No. 5,307,693. Another type of probe operates in a non-contact region 42 located approximately 1 nm from the physical surface. The probe causes the probe tip mounted on the end of a cantilever to oscillate near a natural resonance of the cantilever, typically about 300 Hz. A laser interferometer measures the amplitude of the oscillation. As the probe tip approaches the sample surface in the non-contact region 42, the van der Waals force dampens the oscillation or at least shifts the resonance frequency, as described by Hammond et at. in U.S. Pat. No. 5,262,643 and Flecha et al. in U.S. Pat. No. 5,801,381. Furthermore, once the desired amplitude has been achieved, feedback mechanisms may be used to vertically move the probe rip to keep it oscillating with this amplitude. Thereby, as the tip is laterally scanned over a slowly varying topography, the tip remains positioned at a fixed separation from the surface, thereby profiling the surface. The non-contact probe has the further advantage of not actually contacting the sample, thus avoiding damage to a production wafer although this is less of a problem in probing grating test sites, as well as limiting tip wearing as interaction substrate-tip will be smoother in nature.

The measuring apparatus, as illustrated in FIG. 1, also contains a scatterometer in the form of an ellipsometer. Ellipsometry itself is well known, and commercial ellipsometers are available from, for example, KLA-Tencor Corporation, San Jose, Calif. Aspnes et al. describe the theory and configuration of ellipsometers in U.S. Pat. No. 5,091,320. Azzam and Bashara provide a general description of ellipsometry in the book *Ellipsometry and Polarized Light* (North Holland, Amsterdam, 1977).

According to this embodiment of the invention, the optical components of the ellipsometer are commonly mounted with the AFM on the support structure of the gantry 20 so as to be held in alignment with respect to each other. Unillustrated optics direct an incident light beam 50 from a broad band light source 52 such as a xenon lamp through a oscillating polarizer 54 onto a focusing point at the surface of the wafer 12 held on the wafer pedestal 14. The beam 50 can generally be focused to a beam width of about 40 microns. The oscillating polarizer 54 may be, for example, a rotating Rochon prism or a photoelastic polarizer driven by an oscillatory drive signal. The photoelastic polarizer may include a body of piezoelectric quartz sandwiched between two electrodes.

An ellipsometric optical detector 56 is arranged to receive a reflected beam 58 from the focusing point on the wafer 12. The incident and reflected beams 50, 58 are disposed at complementary angles from a normal to the wafer surface, in the illustrated ellipsometer about 70 degrees. At this angle, the 40 $\mu$m beam width irradiates a spot about 150 $\mu$m long. The large angle is chosen to maximize differences in reflection between the two radiation polarizations. The ellipsometric detector includes a set polarizer, a scanning monochromatic, and an optical detector. The computer 34 controls the monochromer and records the spectrally resolved intensity data, which for dual ellipsometric data, is also resolved according to polarization. Ellipsometers of other designs may be used including those placing the oscillatory polarization analyzer on the reflected beam. Graphs of intensity generated by the ellipsometer are then compared with library graphs. The measured line width is then assumed to be the same as the line width used to generate that particular library graph. Although the example herein describes using a scatterometer to measure line width, the invention is not so limited and the scatterometer could be used to measure other geometric or non-geometric parameters.

The ellipsometric focusing point on the wafer 12 need not be coincident with the probe position underlying the probe tip 30. Because the AFM and the ellipsometer optics are commonly supported, the focusing point and the probe position may be offset by a set, predetermined, and determinable displacement requiring a fixed displacement of the x-direction and y-direction slides 16, 18 and possibly a z-direction slide to move between the testing position of the AFM and that of the ellipsometer. The wafer remains chucked to the pedestal during the movement and during the two types of measurements before and after the movement. Thereby, the same area characterized by scatterometry can be profiled by the atomic force microscopy without the need to find the same area.

As described above, it is necessary to generate accurate library graphs to correctly interpret scatterometer results. The AFM can assist in producing accurate library graphs for determining line width and in verifying that the graphs, which are only accurate for a given surface material, layer thickness, and pitch, are appropriate to the sample being measured.

Library graphs are typically generated by a simulation computer program. It is necessary to provide the simulation program accurate initial information about the pitch and the characteristics of the material. Oftentimes, the pitch information used in a simulation program is the pitch specified by the pattern designer. The actual pitch of the test pattern, however, may vary from the design pitch because of inaccuracies in the photolithograph process that creates the pattern. Using an inaccurate pitch to generate the library graphs results in poor fitting of the measured graphs to the library graphs and inaccurate measurements.

The AFM can scan the test pattern and provide accurate pitch information to be used as input for building the library. Using the accurate pitch measurement from the AFM, a set of library graphs can then be generated by simulating changes in line width. Providing accurate input to the library generation program anchors the simulation results to the actual physical process used to fabricate the measured patterns. After a library is created, the library accuracy can be verified by scanning portions of test patterns with the AFM to check that the scatterometer results determined using the library agree with the dimension found by the AFM.

To measure a scatterometer test pattern with the AFM, either for library generation or for measurement verification, an AFM would typically perform multiple scans at each of multiple locations on the pattern. For example, a beam target circle could be designated, and five AFM scans could be performed at the center of the target circle and at four points spaced along a circumference ten or fifteen microns from the center. Each scan comprises, for example, about 20 scan lines, with each line being 3 $\mu$m long and a distance of about 1 $\mu$m between lines. At least five pitches should be scanned in along the scan line. Skilled persons can readily vary the AFM measurements to adequately measure different targets.

The scatterometer, which rapidly measures the test patterns, can be used to monitor the integrated circuit fabrication process. Because the scatterometer results depend on a large number of parameters, the scatterometer can rapidly monitor and detect process variations that affect any of a large number of parameters. While the scatterometer can specifically identify small changes to a parameter, such as line width, within the limits of the library, and the scatterometer can flag larger changes by failing to match a library graph, the scatterometer cannot typically identify the nature of the quantitative or qualitative changes that are outside the library scope.

The AFM can measure the actual product when a problem is indicated by the scatterometer. The AFM is calibrated to external standards and its geometric measurements are essentially independent of the material being measured. The detailed geometry information available from the AFM could be used to verify that a problem exists with the fabrication process and to identify the nature of the problem. Thus, the scatterometer can screen for a large number of variables and the AFM can be used when the scatterometer flags an anomaly. Using the scatterometer, which measures a site in less than a second and multiple sites on a wafer in a few seconds, as a screening device, obviates the need to measure each site with the AFM, which requires about two minutes to measure a single feature.

Figure 3:
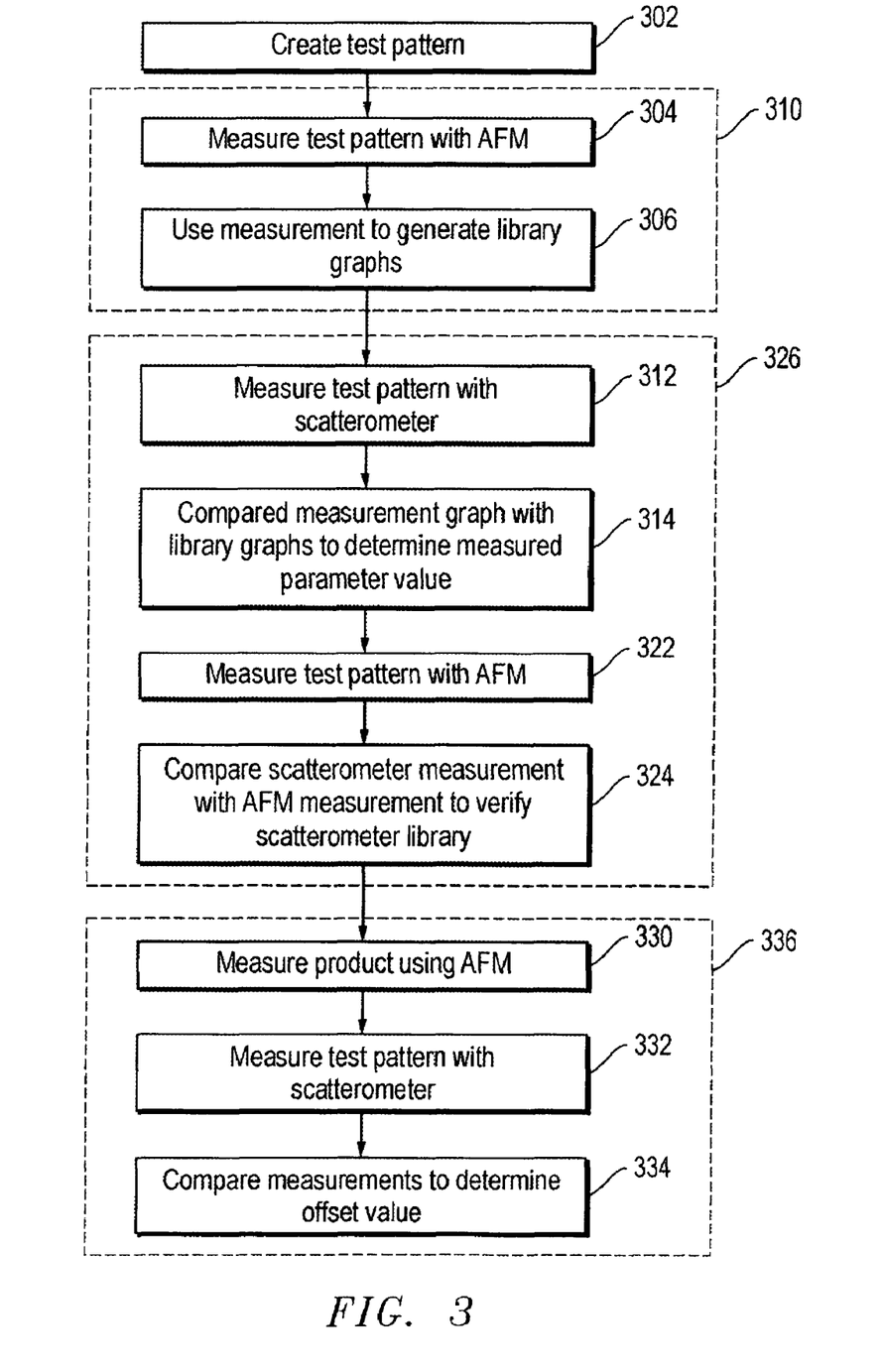
FIG. 3 is a flowchart showing preferred steps for preparing an embodiment of the invention for measuring.

FIG. 3 is a flowchart showing a process for setting up an integrated instrument and monitoring a fabrication process using the integrated instrument. Although the steps below describe single measurements, skilled persons will understand that steps may require multiple measurements across a range of conditions to be statistically valid.

In step 302, while a photolithography process is creating circuit features, the photolithography process also creates test patterns for the scatterometer. In step 304, the test pattern is measured with the AFM to determine a line spacing or pitch. In step 306, a simulation program generated library graphs for the scatterometer using the measured pitch information measured in step 304. Together, steps 304 and 306 comprise a process 310 for creating and anchoring a library.

The library can then be verified. In step 312, a test pattern is measured using the scatterometer and the measured graph is compared in step 314 to library graphs to determine the line width of the test pattern lines. In step 322, a portion of the test pattern is measured using the AFM. In step 324, the line width as determined by the scatterometer is compared to the line width measured by the AFM. If the measurements agree, the library has been shown to be correct for that measurement. If the measurements do not agree, the scatterometer library may need to be regenerated. The scatterometry measurements depend on the optical properties, specifically the index of refraction (n) and the dielectric constant (k), of the material being measured and if these properties vary from the assumed values, the scatterometer will not accurately measure line width. If these properties of the surface differ from the values used in the simulation that created the library graphs, the library graphs will not be accurate and will need to be regenerated using the correct n and k. Steps 322 and 324 can be repeated multiple times for different patterns to statistically validate the library. Steps 312 to 324 constitute a process 326 for validation of the library.

Because the scatterometer measures a test pattern and not the actual product, it is necessary to verify that the test pattern measurements correlate to the dimensions of the actual product. A difference in measurements between the test pattern and the product may occur, for example, because the line width in the test pattern is different from the line width in the actual circuit. Although the test pattern and the circuit features are created at the same time by the same photolithography processes, the results of those processes can vary due to local conditions. For example, it is known that diffraction effects cause the line width produced by a photolithography process to depend in part upon the proximity of other lines, and the lines in the test grating are typically much further apart than the lines on the product. Also, the substrate upon which the line is printed can cause diffraction effects that affect the printing of the line and cause variation in the line width.

The AFM can be used to measure the product to confirm that the test pattern measurement corresponds to the actual product dimensions or to provide an offset value for use with the scatterometer values when necessary. The offset value may be a constant or may vary depending on other processing parameters. In step 330, a portion of a product wafer is measured by the AFM and in step 332, the line width of the product is measured by the AFM. The measurements from steps 330 and 332 are compared in step 334 and if the measurements are different, an offset factor is determined based on the difference. The offset is applied to subsequent measurements of the scatterometer. This offset is based on differences between the line widths on the product and on the test pattern, and is not a result of measurement error of the scatterometer. Steps 330 to 334 constitute a process 336 for compensating for a difference between the test grating and the product.

After the library has been generated and confirmed and the scatterometer has been calibrated, the scatterometer is ready to be used to monitor the fabrication process. As long as the fabrication process is operating properly, the scatterometry results are valid within a small window for which the library provides closely corresponding reference sets of signatures. However, if a site demonstrates a signature that varies significantly from the library being currently used, that same site can be immediately probed by the AFM to provide geometric information.

Figure 4:
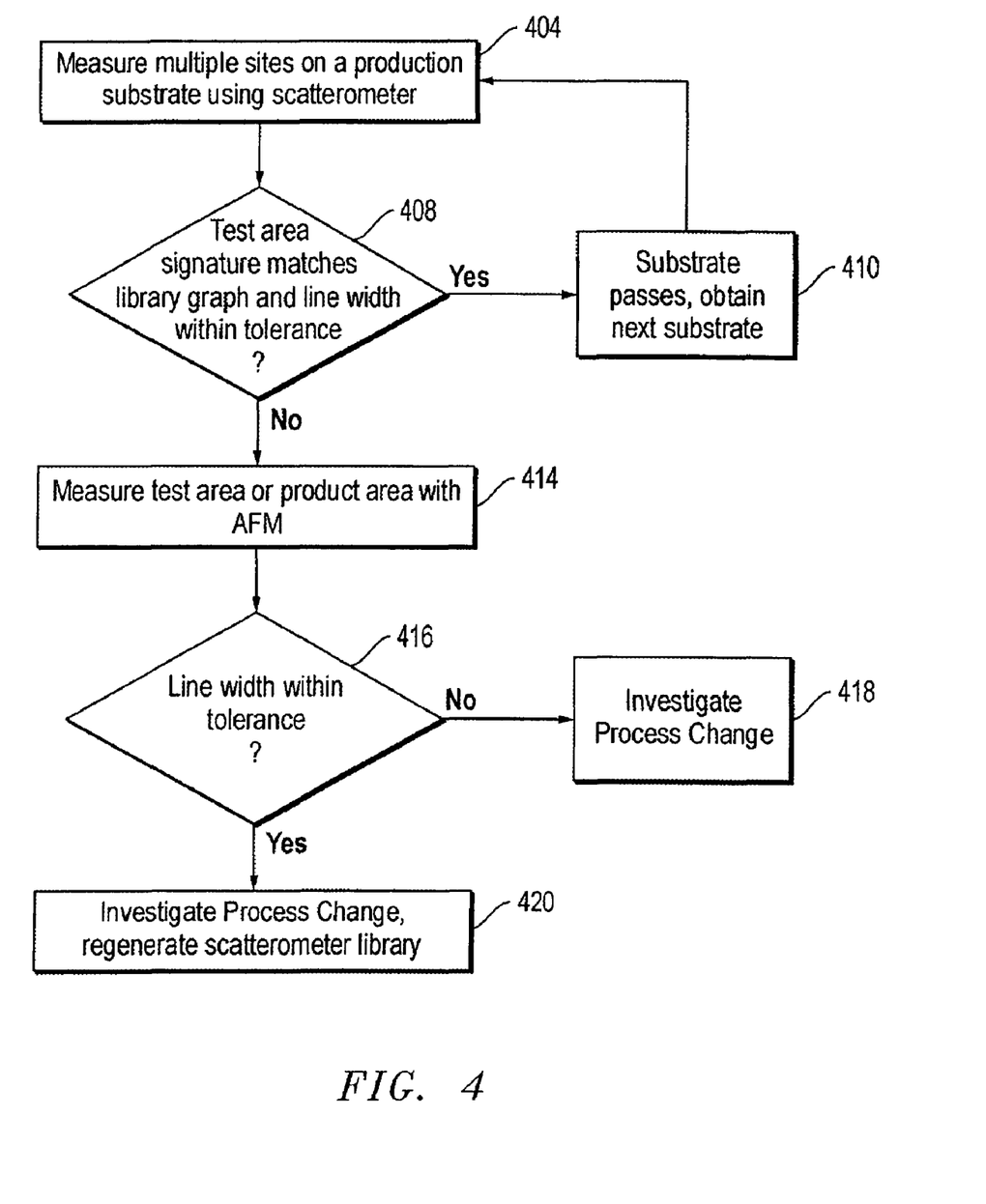
FIG. 4 is a flowchart showing the preferred steps for using an embodiment of the invention to process monitoring.

FIG. 4 shows the steps of using the integrated measuring instrument as a process monitor. In step 404, the scatterometer measures, for example, five grating sites of a wafer going through the production line to create scatterometer graphs for those sites. In step 408, the scatterometer graphs of each site are compared to the library graphs. If the site graphs math library graphs corresponding to a line width within the process control limits, the wafer is passed in step 410 on to the next processing step. If, however, the site scatterometer graphs match library graphs corresponding to line widths outside the process limits, or the sire graphs fail to match a library graph, the test measurement area is measured in step 414 using the AFM to determine whether the grating size has in fact changed, or whether indication by the scatterometer of a lack of process control is caused by a different change in the substrate that causes the assumptions underlying the library to be false.

In step 416, if the AFM measurement shows that the line width is within process limits, a process engineer will investigate in step 418 to determine whether characteristics other than line width, such as the optical properties of the material or the feature profiles, have changed. The process may need to be adjusted or it may be necessary to generate new library graphs to correspond to the changed, but otherwise acceptable conditions. If the line width was not within tolerance in step 416, the process engineer will investigate in step 420 to learn what caused the process to change.

Even when the scatterometer does not indicate a problem, it may be desirable to periodically measure a site, either on the test grating or on a circuit element, using the AFM to obtain a complete three-dimensional geometric characterization of the features and to verify that the scatterometer is measuring correctly.

To obtain the most benefit from the two complementary instruments, the user should understand the fundamentals of each type of measurement. The scatterometer integrates all variations within the relatively large measurement spot of 30 or 40 $\mu$m: The scatterometer reading is a single measurement that represents an average line width/thickness/profile for all lines in the entire area. The AFM scans one or few scan lines, measuring the line width/height/profile at a series of points, and then may scan an adjacent line to cover an area. The AFM can characterize variations within a single structure. Edges of a feature may not be exactly straight, causing variation in line widths. The AFM can be used to characterize line roughness and variation in line edges, whereas the scatterometer will average out all the variations. The AFM can measure the complete three-dimensional profile of a feature, rather than just the top line width.

The AFM not only provides complementary benefits to the scatterometer, the scatterometer also provides benefits to the AFM. The AFM takes a long time to scan a large area. For example, it could take six or eight hours to scan a 50 μm×50 μm area. The scatterometer integrates over a large area and can measure this area in less than a second. By screening wafers, the scatterometer allows many more wafers to be measured and reduces the workload of the AFM, thereby increasing the usable life of the expensive AFM probe tip.

The AFM measurement capability is limited by the size and shape of the tip. For example, if the side angle of the tip is greater than the angle of a trench wall, the AFM tip cannot contact the trench wall and accurately measure the width at certain height positions on the trench wall. The AFM will return a measurement, but it is not valid, being more influenced by the shape of the tip than by the shape of the feature being measured. There may be no indication to the AFM operator, however, that the returned measurements are not valid. The simulation programs that generate scatterometer library graphs, on the other hand, can accurately create graphs that extrapolate to measurements beyond the capable of the AFM tip, even though the AFM was used to provide input into the library and verify it. The scatterometer can be used to indicate when the AFM has reached its limit of accuracy and its measurements are unreliable.

The number of sites per wafer that can be measured with the relatively slow SPM is very limited. For example, the AFM may realistically be limited to measuring five sites per wafer. Because the scatterometer is so much faster, it can perform over 200 measurements in the same time. This allows the scatterometer to perform many more measurements. This increase in sample size can greatly improve the reliability and precision of the measurement statistics.

In order to obtain the most benefit from combining the two measurements, it is necessary to understand the strengths and weaknesses of both forms and the differences in special resolution between the two types of measurements. For example, a width measurement by a scatterometer provides an average width over a large area. A width measurement by AFM can provide the width at several places on the feature. A width measurement on a cross-sectioned wafer using an SEM provides width information at a single point. A CD SEM can measure width at several places along a line.

The scatterometer graph primarily contains information about two directions, an X direction and a vertical or Z direction. The AFM can scan multiple lines to provide information in the X, Y, and Z direction. The AFM can therefore provide information about surface roughness, sidewall angles and roughness, deviation from a straight line of a feature edge. The scatterometer typically measures an area that is about 50 μm by 50 μm, whereas the AFM typically measures an area that is much smaller. Scatterometers are not yet proven to be accurate below about 70 nm, while AFMs have been shown to be accurate to a few nanometers. Scatterometers have difficulty measuring some feature having Z dimensions greater than one micron because of the potential high aspect ratio of these features, whereas the AFM can readily measure such dimensions.

The scatterometer measurements are limited by the available library graphs, so measurements that indicate large deviations from the expected results are typically not interpretable. The AFM measurements are limited by the shape of the probe tip. Each instrument can assist provide information when the other has reached its measurement limits.

The combined instruments can reduce the total cost of owning and operating both instruments. By screening production wafers with the scatterometer, the required number of AFM measurements is reduced, thereby extending the life of the expensive probe tip. The light source of a scatterometer is typically replaced periodically to ensure accurate measurements. When an AFM is used to provide an external accuracy check on the scatterometer, the light source can be used as long as measurements are accurate, and it does not need to be prematurely replaced.

Another advantage of the combined instruments is a more accurate determination of the width of the AFM tip. While pitch, line roughness, and profile measurements (as examples) with an AFM do not require knowledge of the tip width, line width measurement requires an accurate knowledge of the said width. While AFM will feed the library simulation with an accurate pitch (extracted from accurately calibrated piezo using available standards from NIST or VLSI as examples), scatterometry will use accurately defined wavelength interaction to determine line width from the simulation. Subsequently scanning an area where line width was defined by scatterometry and pitch defined by AFM will allow determination of tip width, thus improving repeatability and accuracy of AFM.

Figure 5:
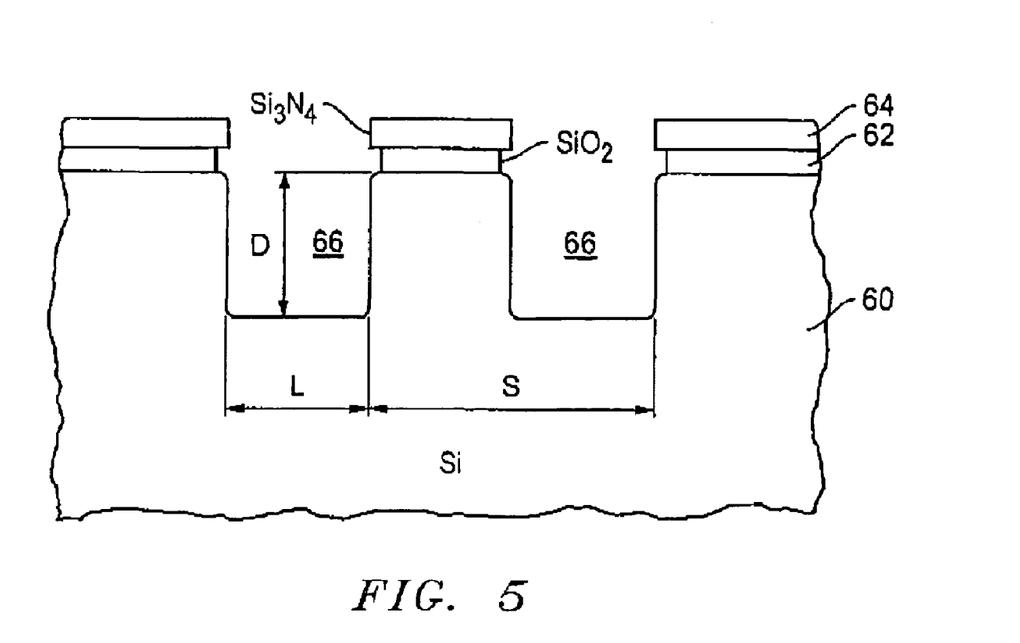
FIG. 5 is a cross-sectional view of art integrated circuit structure to which the invention can advantageously be applied.

The integrate instrument is advantageously used, for example, to monitor the process associated with a trench structure, illustrated in the cross-sectional view of FIG. 5, used in the fabrication of dynamic random access memories (DRAMs). A silicon wafer 60 is covered with patterned layers 62 and 64 of silicon dioxide and silicon nitride, which serve as a hard mask for etching the underlying silicon to form trenches 66. In a series of steps not to be described, large DRAM capacitors are formed on the walls and bottom of the trenches 66. The processes for depositing the $SiO_2$ and $Si_3N_4$ layers 62, 64 and for etching the silicon trenches 66 need to be controlled.

An AFM is effective at measuring variations in the trench spacing S and the trench width L, whether measured on actual trenches or on correspondingly configured test gratings having a large number of such trenches 66 arranged in parallel in a fixed direction and with fixed values of L and S. The AFM however, is ineffective at measuring the thicknesses of the layers 62 and 64 or at separating these thicknesses from the trench depth D. On the other hand, ellipsometry is effective at measuring small variations in the thicknesses of the layers 62 and 64 and of their compositions, at least as manifested in their optical constants n and k. As a result, the combination of an AFM and ellipsometer enables the complete characterization of the structure and composition of the trench structure of FIG. 5. Insofar as the trench parameters affect the ellipsometry analysis, the AFM-measured parameters can be used to narrow the scope of the library used in scatterometry.

The previously described ellipsometer is designed for beams arranged at 70 degrees from the wafer normal. This large angle is chosen to maximize the differences between the two radiation polarizations. However, the large angles also lengthen the maximum dimension of the probe beam on the sample surface from, for example, 40 μm to 150 μm. Such large sampling areas are disadvantageous for integrated circuit manufacturing in which the test sites are located in the kerf or cleave area between dies. For high productivity, the kerf or cleave area should be minimized. Therefore, in some applications in semiconductor process control, it is advantageous to use an ellipsometer for which the beams are arranged at a small angle of less than 10° from the wafer normal, for example, 2° or a reflectometer normal to the surface.

In an ellipsometer, the differences between the two light polarizations are much reduced at low angles. Indeed, such low-angle ellipsometry is considered impossible with isotropic surfaces. However, grating test structures used in semiconductor process control provide significant anisotropy in known directions. Further, the reduced sensitivity of 2 degree ellipsometry can be compensated by using the previously described photoelastic polarizer, which can be cycled at greater than 10 kHz or even 50 kHz and higher, in contrast to the typical 100 Hz cycling rate of rotating polarizers. At the greatly increased polarization cycling rate, a large number of polarization data points can be acquired in a reasonably short time and then averaged to provide greater resolution in separating the two polarization states.

The test equipment of the invention can also be applied to monitor another problem in semiconductor processing. Reactive ion etching of narrow, anisotropic trenches and via holes in oxide often uses a passivation film formed on the sidewalls to prevent excessive anisotropic etching. Ashing or other techniques are applied after etching to assure that the film is removed. Organic contaminants can also originate from the photoresist used in photolithographic etching of any device material. An ellipsometer operating with infrared light in the wavelength band of 5 $\mu$m to 16 $\mu$m is capable of detecting whether any such organic polymer remains. The infrared ellipsometer can be combined with an atomic force microscope in order to detect an organic polymer used, for example, as a passivation film.

While AFMs are very useful for monitoring a full profile of a feature, they are considered too slow to perform at a number of test sites on every wafer. A critical dimension scanning electron microscope (SEM) is quite suitable for a fairly precise determination of line widths, but the critical dimension returned is the width of the feature or test pattern apparent from the top.

Accordingly, another advantageous combination of surface characterization tools is a scatterometer and a SEM integrated on a single platform with a common specimen stage. As illustrated in the schematic side view of FIG. 6, the wafer 12 is supported on the pedestal 14 and its movable stages 16, 18, all located in a vacuum chamber 70 pumped to a vacuum of about $10^{-5}$ to $10^{-8}$ Torr by a vacuum pumping system 72. The vacuum is required for the low-energy electron microscopy of SEMs for which the electron energy is only a few kilovolts. A negatively biased Schottky emitter 74 emits electrons to a grounded anode 76. An aperture 78 forms the accelerated elections into a slightly divergent electron beam 80 approximately normal to the surface of the wafer 12. A coil-driven magnetic lens 82 and an electrostatic lens 84 focuses the beam 80 at surface of the wafer 12. The resultant electrons ejected from the wafer 12 are detected by an electron detector 86, and the electron intensity as the x-y stage 14 under the control of the computer scans the wafer 12 past the focused beam provides an image of the wafer surface. Both low-energy secondary electrons and back-scattered (inelastically scattered) electrons can be used separately or in combination to produce an image. Such SEMs are commercially available and widely used for in-line metrology in integrated circuit fabrication lines.

Figure 6:
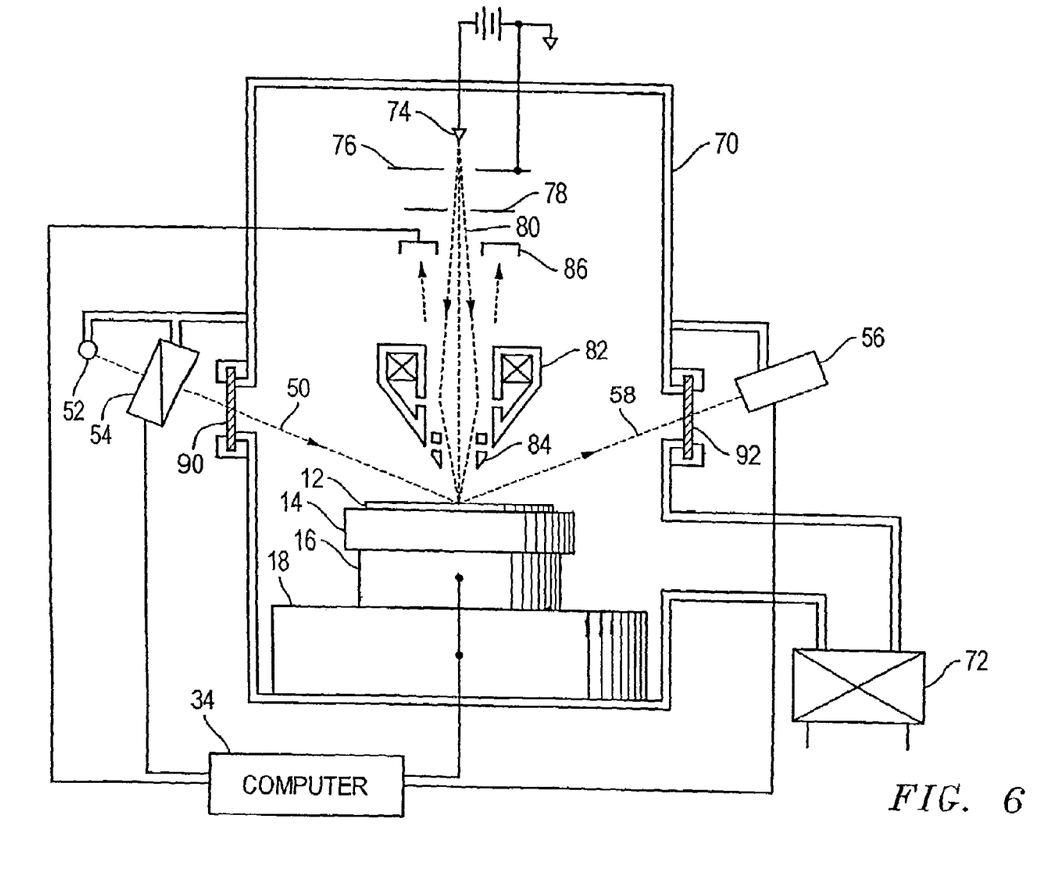
FIG. 6 is a schematic elevational view of a surface analyzer of another embodiment of the invention incorporating both a scatterometer and a critical-dimension scanning electron microscope.

The vacuum chamber 70 includes two optical vacuum ports with windows 90, 92 allowing the ellipsometer input beam 50 to enter the chamber and strike the wafer 12, and be reflected at an equal angle into the output beam 58 which exits the chamber 70, thereby permitting the ellipsometer parts 52, 54, 56 to be located outside the chanter 70 but rigidly mounted thereto.

Similarly to the integrated tool of FIG. 4, the integrated scatterometer and SEM allows the scatterometer to quickly monitor multiple test patterns on every wafer being processed. Periodically, or whenever the signatures do not match the current library, the SEM can be used to immediately provide a complete surface image of the test pattern with no need to realign the wafer to the SEM. Like the AFM, the SEM can also be used to determine to provide accurate pitch information for the simulation program that generates the scatterometer library.

As described above, CD SEM measurements are adversely affected by edge blurring caused by electrical charging of the feature edges. This blurring is difficult to accurately compensate because it is dependent upon the composition and thickness of a number of the layers underlying the feature. In the present invention, the CD SEM edge blurring can be compensated using measurements from the scatterometer, because scattered light is not influenced by electrical charging. Scatterometer repeatability has been shown to be in the 1 nm range. Although the CD SEM can determine the absolute position of an edge to within only about 5 nm on each side, variations in edge positioning in the 1 nm range can be detected by the CD SEM. CD AFM can also determine edge positioning within the 1 nm range. Because the scatterometer is measuring the same wafer as the CD SEM, the compensation determined is appropriate for the particular wafer. The edge blur compensation can be recalculated as necessary, when the composition and thickness of a number of the layers underlying the feature changes.

The overall resolution limitation of the scatterometer is limited by wavelength used, which is typically currently between 193 nm to 850 nm when used in air. Smaller wavelengths, for example, down to 140 nm could be used in a vacuum or Nitrogen. The combination of scatterometry with a charged particle beam system requiring a vacuum environment provides the ability to use wavelengths smaller than 193 nm, for example, as low as 140 nm, allowing scatterometry to improve overall resolution below the actual 70 nm limit.

Although the present invention and its advantages have been described in detail, it should be understood that various changes, substitutions and alterations can be made herein without departing from the spirit and scope of the invention as defined by the appended claims. For example, the integrating optical instrument and the individual feature measuring instrument could be arranged in a cluster, with a material handler moving the work piece from one instrument to the other. The examples describe the use of the instruments to measure dimensions, but the instrument can also measure other characteristics, such as surface composition. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include

We claim as follows:

1. A method of using an integrated scatterometer and atomic force microscope to monitor a fabrication process, comprising:
   mounting a work piece in work piece holder in a single system that includes both an atomic force microscope and a scatterometer;
   measuring a feature in a test measurement area using the atomic force microscope;
   generating scatterometer library graphs using the atomic force microscope measurement as input to a library generation program;
   measuring a test measurement area on the work piece using the scatterometer and the generated library graphs to determine a measured parameter of the measurement area; and
   if the measured parameter fails to meet a specified criterion, measuring one or more features of the work piece using the atomic force microscope without removing the work piece from work piece holder of the single system, thereby allowing features in the area measured by the scatterometer to be readily measured on the atomic force microscope if the scatterometer results are outside of specification or indeterminate and allowing the atomic force microscope to provide input for the generation of accurate library graph for use with the scatterometer.

2. A method of monitoring a fabrication process, comprising:
   mounting a work piece in work piece holder in a single system that includes both an integrating optical instrument and an individual-feature-measuring instrument;
   measuring a test measurement area on the work piece using the integrating optical instrument to determine a measured parameter of the measurement area; and
   if the measured parameter fails to meet a specified criterion, measuring one or more features of the work piece using the individual-feature-measuring instrument without removing the work piece from the single system.

3. The method of claim 2 in which measuring one or more features of the work piece using the individual-feature-measuring instrument includes measuring the one or more features without removing the work piece from the work piece holder.

4. The method of claim 3 in which measuring one or more features of the work piece using the individual-feature-measuring instrument includes measuring the one or more features without moving the work piece from the position at which it was measured using the integrating optical instrument.

5. The method of claim 3 in which measuring one or more features of the work piece using the individual-feature-measuring instrument includes moving the work piece holder a predetermined distance from the position at which it was measured using the integrating optical instrument.

6. The method of claim 2 in which measuring one or more features of the work piece using the individual-feature-measuring instrument includes measuring one or more features in the test measurement area.

7. The method of claim 2 in which measuring one or more features of the work piece using the individual-feature-measuring instrument includes measuring one or more features in a product area.

8. The method of claim 2 in which measuring a test measurement area on the work piece using the integrating optical includes measuring a test measurement area using a scatterometer.

9. The method of claim 2 in which measuring a test measurement area on the work piece using the integrating optical includes measuring a test measurement area using an ellipsometer or a reflectometer.

10. The method of claim 2 in which measuring one or more features of the work piece using the individual-feature-measuring instrument includes measuring a portion of the work piece using a scanning profile microscope or a charged particle beam instrument.

11. The method of claim 10 in which measuring one or more features of the work piece using the individual-feature-measuring instrument includes measuring a portion of the work piece using an atomic force microscope operating in a mode in which a probe tip is moved vertically to contact the work piece surface.

12. The method of claim 2 in which:
    measuring one or more features of the work piece using the individual-feature-measuring instrument includes measuring one or more features of the work piece using an atomic force microscope in which a probe tip is moved vertically to contact the work piece surface; and
    measuring a test measurement area on the work piece using the integrating optical instrument includes measuring a test measurement area with a scatterometer.

13. The method of claim 2 further comprising:
    measuring a test site using the individual-feature-measuring instrument to provide input to a program that generates characterization graphs for use in interpreting the measurement results of the integrating optical instrument; and
    generating characterization graphs for use in interpreting the results of the integrating optical instrument.

14. The method of claim 13 in which generating characterization graphs includes generating characterization graphs comprising scatterometer graphs correlated to line pitch or line width.

15. The method of claim 2 in which measuring a test measurement area on the work piece using the integrating optical instrument to determine a measured parameter of the measurement area includes measuring a test measurement area on the work piece using the integrating optical instrument to determine a geometric parameter of the measurement area and further comprising:
    measuring a geometric parameter of a product feature on the work piece using the individual-feature-measuring instrument;
    comparing the measured geometric parameter of the product feature measured by the individual-feature-measuring instrument with the corresponding geometric parameter of the test pattern measured by the integrating optical instrument;
    if the measured parameters of the product feature determined by the individual-feature-measuring instrument and the measured parameter of the test area determined by the integrating optical instrument are not the same, determining based on the difference between the two measurements a measurement parameter offset between test pattern measurements and product feature measurements; and
    determining a dimension of product feature by measuring the test area using the scatterometer and applying the offset to a test area measurement.

16. A integrated measuring system, comprising:
a work piece holder for holding a sample to be measured;
an integrating optical instrument having a radiation source for irradiating an area of said work piece and an optical detector receiving radiation reflected from said area; and
an individual-feature-measuring instrument for measuring the same work piece as measured by the integrating optical instrument, the individual-feature-measuring instrument being positioned in the same system as the integrating optical instrument so that the same work piece can be readily measured by both instruments.

17. The system of claim 16 in which the integrating optical instrument and the individual-feature-measuring instrument are positioned such that the area measured by the integrating optical instrument encompasses the area measured by the individual-feature-measuring instrument without repositioning the work piece.

18. The system of claim 16 in which the integrating optical instrument and the individual-feature-measuring instrument are positioned such that the area measured by the integrating optical instrument is offset by a predetermined distance Thorn the area measured by the individual-feature-measuring instrument, thereby allowing the work piece holder to be repositioned by a predetermined amount when switching between the two measuring instruments.

19. The system of claim 16 in which the integrating optical instrument comprises a scatterometer.

20. The system of claim 16 in which the integrating optical instrument comprises a scatterometer and the individual-feature-measuring instrument comprises an atomic force microscope.

21. The system of claim 16 in which the individual-feature-measuring instrument includes a charged particle beam instrument or an atomic force microscope.

22. The system of claim 16 and the integrating optical instrument comprises an ellipsometer or a reflectometer.

23. The system of claim 16 in which the radiation source projects a beam toward the work piece at an angle of incidence of less than 10 degrees and further comprising a polarization analyzer along the optical path of the beam after reflection from the work piece.

24. The system of claim 16 further comprising a transfer mechanism for moving the work piece between the integrating optical instrument and the individual-feature-measuring instrument.

25. The system of claim 16 in which the integrating optical instrument measures and the individual-feature-measuring instrument are configured to determine through different measuring techniques the same characteristic of the work piece.

26. The system of claim 25 in which the integrating optical instrument measures and the individual-feature-measuring instrument are configured to determine line width or line spacing, wherein the integrating optical instrument determine an average line width or line spacing and the individual-feature-measuring instrument determines one or more individual line widths or line spacings.

27. A method of generating library information for interpreting the results of integrating optical instrument measurements, comprising:
fabricating a pattern on a work piece;
determining a measurement parameter by measuring part of the pattern using an individual-feature-measuring instrument;
generating library information for interpreting the results of integrating optical instrument measurements by using the determined measurement parameter as input to a library information generation program; and
wherein the step of determining a measurement parameter by measuring part of the pattern using an individual-feature-measuring instrument includes measuring a dimension using an individual-feature-measuring instrument having a measurement target area within an illumination area of an integrated optical instrument of the type for which the library information generation program generates library information.

28. The method of claim 27 in which determining a measurement parameter by measuring the pattern using an individual-feature-measuring instrument includes measuring a dimension using an individual-feature-measuring instrument having a work piece holder maintaining a work piece within the measurement area of the individual-feature-measuring instrument and within the measurement area of an integrated optical instrument of the type for which the library information generation program generates library information without moving the work piece or by moving the work piece a predetermined amount.

29. The method of claim 27 further comprising:
determining a measurement parameter by measuring the pattern using the integrating optical instrument; and
comparing the value of the measurement parameter as determined by the integrating optical instrument with the value of the measurement parameter determined by the individual-feature-measuring instrument to verify that the accuracy of the library graphs.

30. The method of claim 27 in which:
determining a measurement parameter by measuring the pattern using an individual-feature-measuring instrument includes determining a measurement parameter by measuring the pattern using an atomic force microscope; and
generating library information for use with an integrated optical instrument using the determined measurement parameter as input to a library information generation program includes generating library information for use with a scatterometer.

31. The method of claim 27 in which determining a measurement parameter by measuring the pattern using an individual-feature-measuring instrument includes determining line pitch or line width.

32. The method of claim 27 determining a measurement parameter by measuring a pattern includes determining a measurement parameter by measuring a test pattern using an individual-feature-measuring instrument and further comprising:
measuring a measurement parameter on a product;
comparing the measurement parameter measured on the product with the measurement parameter measured on the test pattern to determine whether there is a difference, and if so, determining an offset to apply to test pattern measurements to determine product measurements.

* * * * *